United States Patent
Chalupper

(10) Patent No.: US 9,775,999 B2
(45) Date of Patent: Oct. 3, 2017

(54) SYSTEM COMPRISING A COCHLEAR STIMULATION DEVICE AND A SECOND HEARING STIMULATION DEVICE AND A METHOD FOR ADJUSTMENT ACCORDING TO A RESPONSE TO COMBINED STIMULATION

(71) Applicant: ADVANCED BIONICS AG, Staefa (CH)

(72) Inventor: Josef Chalupper, Paunzhausen (DE)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/909,973

(22) PCT Filed: Aug. 9, 2013

(86) PCT No.: PCT/EP2013/066744
§ 371 (c)(1),
(2) Date: Feb. 3, 2016

(87) PCT Pub. No.: WO2015/018457
PCT Pub. Date: Feb. 12, 2015

(65) Prior Publication Data
US 2016/0175591 A1    Jun. 23, 2016

(51) Int. Cl.
*A61N 1/36* (2006.01)
*A61B 5/12* (2006.01)
(Continued)

(52) U.S. Cl.
CPC .......... *A61N 1/36032* (2013.01); *A61B 5/123* (2013.01); *A61B 5/16* (2013.01);
(Continued)

(58) Field of Classification Search
CPC ... A61N 1/36032; H04R 25/70; H04R 25/353
See application file for complete search history.

(56) References Cited

U.S. PATENT DOCUMENTS

| 3,221,100 A | 11/1965 | Towne |
|---|---|---|
| 8,155,747 B2 | 4/2012 | Faltys et al. |

(Continued)

FOREIGN PATENT DOCUMENTS

| WO | WO-2005/097255 | 10/2005 |
|---|---|---|
| WO | WO-2006/053101 | 5/2006 |
| WO | WO-2011/032021 | 3/2011 |

OTHER PUBLICATIONS

International Search Report and Written Opinion received in International Application No. PCT/EP2013/066744, dated Feb. 24, 2014.
(Continued)

*Primary Examiner* — Alyssa M Alter
(74) *Attorney, Agent, or Firm* — ALG Intellectual Property, LLC

(57) ABSTRACT

There is provided a system comprising a first device for neural stimulation of a cochlea of a patient's ipsilateral ear; a second hearing stimulation device selected from the group consisting of a device for neural stimulation of the cochlea of the patient's contralateral ear, a device for acoustic stimulation of the patient's ipsilateral ear and a device for acoustic stimulation of the patient's contralateral ear and comprising means for stimulation of the respective ear; and a fitting device for adjusting at least one of the first stimulation device and the second stimulation device according to a response of the patient to combined stimulation by the first stimulation device and the second stimulation device.

28 Claims, 6 Drawing Sheets

(51) Int. Cl.
*H04R 25/00* (2006.01)
*A61B 5/16* (2006.01)

(52) U.S. Cl.
CPC .......... *H04R 25/353* (2013.01); *H04R 25/70* (2013.01); *H04R 2225/43* (2013.01); *H04R 2225/81* (2013.01)

(56) References Cited

U.S. PATENT DOCUMENTS

| | | |
|---|---|---|
| 8,295,937 B2 | 10/2012 | Fridman et al. |
| 2005/0261748 A1 | 11/2005 | van Dijk |
| 2011/0218592 A1 | 9/2011 | Svirsky |
| 2011/0238176 A1 | 9/2011 | Bradley et al. |
| 2011/0280424 A1 | 11/2011 | Takagi et al. |
| 2013/0004000 A1 | 1/2013 | Franck |
| 2013/0101123 A1 | 4/2013 | Hanneman |

OTHER PUBLICATIONS

Kong, Y. Y. et al., "Cross-frequency Integration for Consonant and Vowel Identification in Bimodal Hearing", *J. Speech Lang. Hear. Res. 2011*, 54(3), pp. 959 to 980.

Svirsky, M. et al., "Integration of Vowel Identification Cues in Listeners with a Cochlea Implant and a Hearing Aid", *Poster at IHCON 2012*.

Yoon, Y. et al., "Binaural benefit for speech recognition with spectral mismatch across ears in simulated electric hearing", *J. Acoust. Soc. Am. 130*(2), 2011, pp. 94 to 100.

Carlyon, R. et al., "Pitch comparison to an electrical stimulation of a cochlear implant and acoustic stimuli presented to a normal-hearing contralateral ear", *JARO 11*, 2010, pp. 625 to 640.

James, C. et al., "Contralateral masking in cochlear implant users with residual hearing in the non-implanted ear", *Audiology & Neuro-Otology 6*, 2011, pp. 87 to 97.

SYSTEM COMPRISING A COCHLEAR STIMULATION DEVICE AND A SECOND HEARING STIMULATION DEVICE AND A METHOD FOR ADJUSTMENT ACCORDING TO A RESPONSE TO COMBINED STIMULATION

The invention relates to a system comprising a first device for neural stimulation of the cochlea of one ear, a second device for acoustic stimulation of the same ear or the other ear or for neural stimulation of the cochlea of the other ear and a fitting device for individually adjusting the first and/or second stimulation device to the patient.

Typically, cochlear implants comprise an electrode array for electrical stimulation of the cochlear at various stimulation sites determined by the position of the respective electrode. Systems for bimodal stimulation of the hearing comprise a cochlear implant at the ipsilateral ear and a device for acoustic stimulation of the ipsilateral ear or the contralateral ear. Systems with electric and acoustic stimulation of the same ear are also known as hybrid devices or EAS devices. In systems with contralateral acoustic stimulation the acoustic stimulation device typically is an (electro-acoustic) hearing aid.

For optimal fitting of such bimodal systems knowledge about the location of the electrodes of the electrode array with regard to the cochlea after surgery is an important prerequisite.

In principle, the electrode location could be determined via CT (computed tomography) scans. However, such a method would be expensive and would require an additional appointment for the patient in another clinical department, and also there would be an additional radiation dose which is difficult to justify except for a diagnostic test directly impacting the patient's health.

A more practical approach is to use behavioral pitch matching for determining the pitch and the electrode location. An example of such procedure is discussed in the article "*Pitch comparison to an electrical stimulation of a cochlear implant and acoustic stimuli presented to a normal-hearing contralateral ear*" by R. Canyon et al., in JARO 11, 2010, pages 625 to 640, wherein either pure tones or filtered harmonic complexes are presented to the normal hearing ear as acoustic stimuli and electric stimuli are presented as biphasic pulse trains in monopolar mode to one electrode, with the acoustic stimuli and the electric stimuli being presented simultaneously or subsequently to the patient. Unfortunately, such pitch matching procedure is very tedious and unreliable.

According to the article "*Contralateral masking in cochlear implant users with residual hearing in the non-implanted ear*" by C. James et al., Audiology & Neuro-Otology 6, 2011, pages 87 to 97, threshold elevations for electrical stimulation probes were observed when acoustic contralateral maskers were presented; the acoustic masking signals were tones or narrow band noise signals.

US 2005/0261748 A1 relates to a fitting method for a hybrid device used by a patient having residual acoustic hearing capability at the ipsilateral ear, wherein the portion of the cochlea having residual acoustic hearing capability is determined by measuring the neural response to acoustic and/or electrical stimulation. Acoustic background noise, in particular narrow band background stimulus of a frequency substantially corresponding to the position of the tip electrode, is applied together with an electrical stimulus in order to determine from ECAP measurements which portion of the cochlear has residual acoustic hearing capability, with the ECAP measurements being used to determine a frequency-electrode position map.

US 2011/0238176 A1 likewise relates to a fitting method for a hybrid device, wherein a tonotopic response for the residual hearing of the ipsilateral cochlear is measured to obtain a place-frequency map, the cochlear implant (CI) is inserted according to the place-frequency map, and the position of the CI then is confirmed according to the measured place-frequency map via the measurement of the evoked neural response, such as the auditory brainstem response (ABR), to electrical stimulation of the CI and simultaneous acoustic stimulation. The acoustic stimulus is a customized chirp signal.

WO 2006/053101 A1 relates to a bilateral CI system, wherein pitch information is matched between the two CI devices by utilizing virtual electrodes, with at least one electrode of the electrode array of one ear being mapped to a virtual electrode of the electrode array of the other ear.

U.S. Pat. No. 8,155,747 B2 relates to a method of fitting a bilateral hearing system comprising a CI device at one ear and a hearing aid at the other ear.

U.S. Pat. No. 8,295,937 B2 relates to a method of fitting a CI device by using a harmonics-based tuner for aligning the band pass filters associated with each implanted electrode contact.

The article "Cross-frequency Integration for Consonant and Vowel Identification in Bimodal Hearing" by Y.-Y. Kong et al., in J. Speech Lang. Hear. Res. 2011, 54(3), pages 959 to 980, relates to a study on the ability of CI users to integrate speech cues across frequencies, according to which speech cues extracted from the CI device and a hearing aid are highly redundant for consonants but complementary for vowels.

A similar study is described in "Integration of Vowel Identification Cues in Listeners with a Cochlea Implant and a Hearing Aid" by M. Svirsky et al., Poster at H-ICON 2012.

The article "Binaural benefit for speech recognition with spectral mismatch across ears in simulated electric hearing" by Y. Yoon, et al., J. Acoust. Soc. Am. 130(2), 2011, pages 94 to 100, relates to a study investigating the effects of binaural spectral mismatch on binaural benefits in the context of bilateral cochlea implants using acoustic stimulations.

US 2011/0218592 A1 relates to a method of obtaining individualized frequency-to-electrode maps in a CI device.

In general, for achieving full benefit of the bimodal or bilateral stimulation in CI systems with bimodal and/or bilateral stimulation it is important that there is a good pitch matching across the two stimulation devices.

It is an object of the invention to provide for a system comprising a CI device, a second hearing stimulation device and a fitting device, wherein bimodal and/or bilateral reception is optimized with regard to the integration of stimuli from the two devices.

It is a further object to provide for a corresponding method of individually adjusting a CI device and a second hearing stimulation device.

According to the invention, these objects are achieved by a system as defined in claim 1 and a method as defined in claim 24, respectively.

The invention is beneficial in that, by using a probe neural stimulation signal and a second stimulation signal which are supplied in a synchronized manner to the patient via the first stimulation device and the second stimulation device, respectively, and which are designed in such a manner that they are recognized by the patient as carrying a target speech information in case that the patient is able to fuse or merge the stimuli reciting from the signals into a single percept, with the target speech information being divided onto the two signals and with the signals not carrying the target speech information when perceived separately by the patient, optimized parameter settings of the two devices can be obtained in an iterative process, in particular with regard to pitch matching of the hearing stimulation by the first stimulation device and the second stimulation device. In particular, the iteration loop may be repeated until pitch matching is achieved to an extent that the patient is able to fuse the stimuli from the first device and from the second device.

The second device may be a device for acoustic stimulation of the ipsilateral ear or the contralateral ear or a CI device for stimulation of the contralateral ear.

Preferably, the target speech information is divided onto the probe neural stimulation signal and the second probe stimulation signal by allocating a first spectral region to the second probe stimulation signal only and a second spectral region to the probe neural stimulation signal only, wherein the first spectral region preferably corresponds to a first formant of a vowel and the second spectral region corresponds to a second formant of the vowel (in addition to such first and second spectral region which are allocated to only one of the probe neural stimulation signal and the second probe stimulation signal, respectively, there may be also a third spectral region which is allocated to both the probe neural stimulation signal and the second probe stimulation signal, i.e. there may be a spectral region in which there is some kind of overlap in the stimulation).

Preferably, in case that the second stimulation device is an acoustic stimulation device, the first spectral region is at lower frequencies than the second spectral region, i.e. the first formant is supplied via the acoustic stimulation device and the second formant is supplied via the CI device.

Further preferred embodiments are defined in the dependent claims.

Hereinafter, examples of the invention will be illustrated by reference to the attached drawings, wherein.

Figure 1:
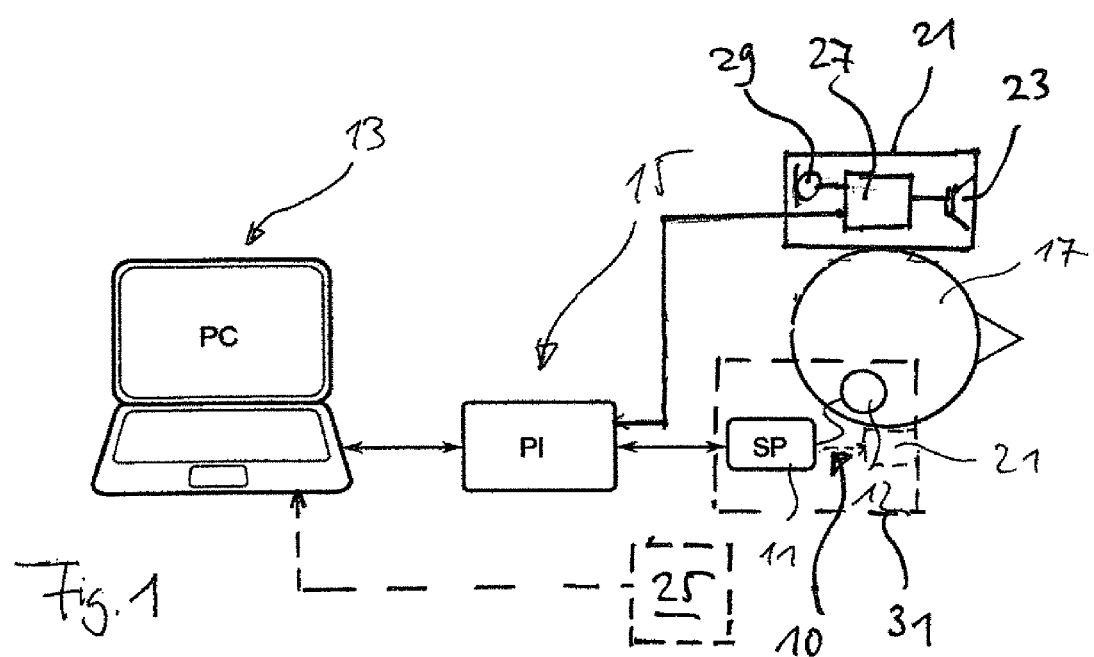
FIG. 1 is a schematic representation of an example of a system according to the invention.

FIG. 1 is a schematic representation of an example of a bimodal stimulation system according to the invention, comprising a fitting/programming unit 13, which may be implemented as a computer, a programming interface 15, a CI device 10 comprising a sound processing subsystem 11 and an implantable stimulation subsystem 12 and being worn by a patient 17 at the ipsilateral ear, and a hearing aid 21 worn at the contralateral ear and comprising a loudspeaker 23 for acoustic stimulation of the contralateral ear. The programming unit 13 communicates with the sound processing subsystem 11 and with the hearing aid 21 via the programming interface 15, which may be implemented as a wired or wireless connection.

The programming unit 13 serves to control the sound processing subsystem 11 of the CI device 10 such that probe neural stimulation signals are applied to the ipsilateral ear of the patient 17 via the stimulation subsystem 12 and to control the hearing aid 21 such that probe acoustic stimulation signals are presented via the loudspeaker 23 to the contralateral ear of the patient 17 in a synchronized manner with regard to the probe neural stimulation signals. The perceptual behavioral response of the patient 17 to the such synchronized stimulation is recorded by the programming unit 13 via a user interface, which may be part of the programming unit (such as the computer keyboard) or may be provided separately (as schematically indicated at 25 in FIG. 1). The patient's response then is used in programming the sound processing subsystem 11 in order to fit the CI device 10 and the hearing aid 21 as a bimodal system to the patient 17.

It is to be understood that the programming unit 13 is used with the CI device 10 and the hearing aid 21 only for adjustment/fitting, but not during normal operation of the CI device 10 and the hearing aid 21.

In case that the fitting/programming unit 13 is adapted to generate audio signals/stimulation signals on its own, in case that the fitting/programming unit 13 includes a signal generator unit, the programming interface 15 may be replaced by an audio interface for supplying the audio signals generated by the fitting/programming unit 13 to the CI device and the hearing aid 21.

Alternatively or in addition, a signal generator may be included in the CI device 10 and/or the hearing aid 21; in this case the fitting/programming unit 13 includes a unit which provides for synchronization (preferably wireless) or at least synchronized triggering of such internal signal generator(s) of the CI device 10 and/or the hearing aid 21, i.e. a unit which controls such internal signal generators in an appropriate manner.

Figure 2:
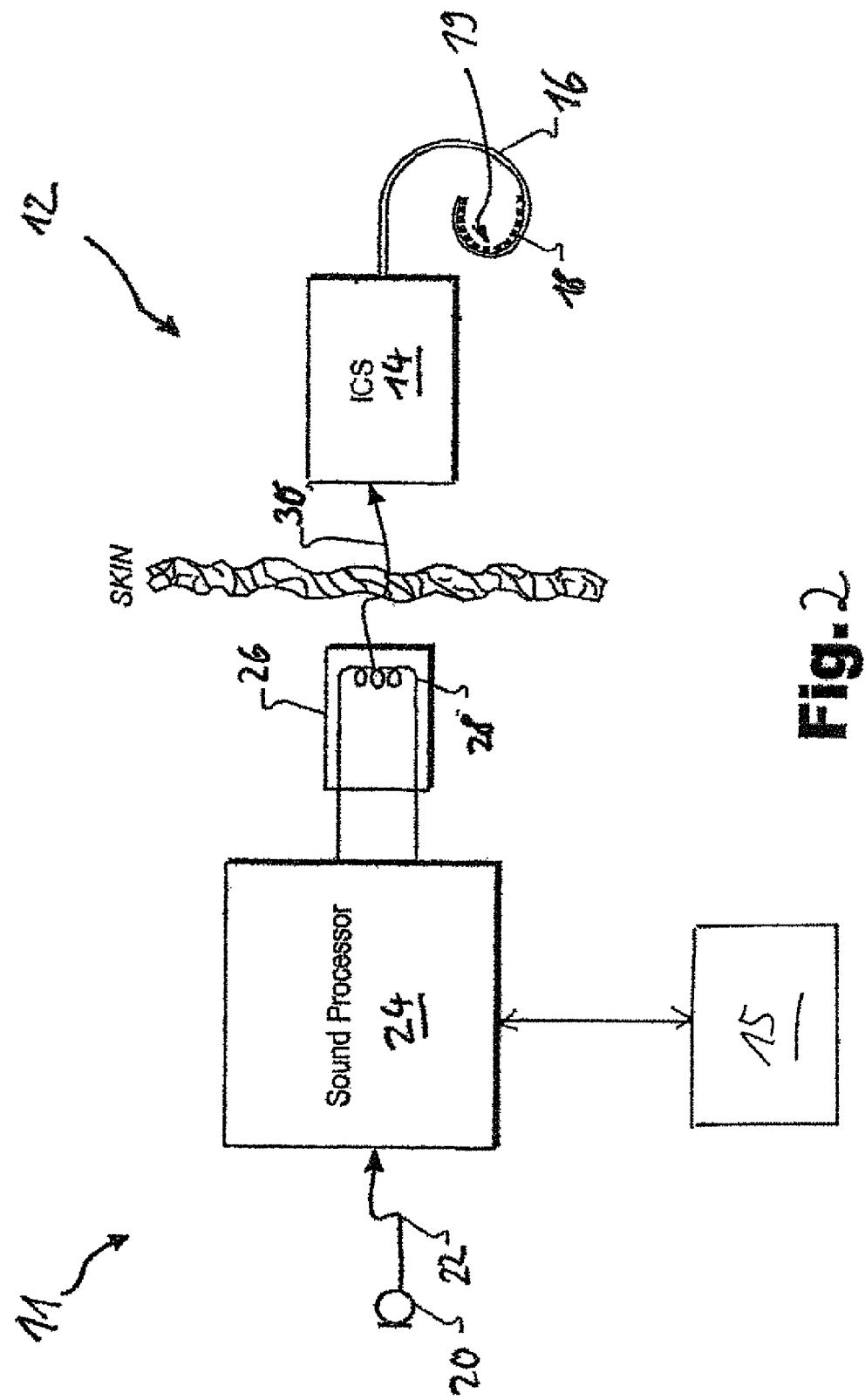
FIG. 2 is a schematic representation of an example of the CI device of FIG. 1.

In FIG. 2 an example of the cochlear implant device 10 of the system of FIG. 1 is shown schematically. The sound processing sub-system 11 serves to detect or sense an audio signal and divide the audio signal into a plurality of analysis channels, each containing a frequency domain signal (or simply "signal") representative of a distinct frequency portion of the audio signal. A signal level value and optionally a noise level value are determined for each analysis channel by analyzing the respective frequency domain signal, and a noise reduction gain parameter may be determined for each analysis channel as a function of the signal level value and the noise level value of the respective analysis channel. Noise reduction may be applied to the frequency domain signal according to the noise reduction gain parameters to generate a noise reduced frequency domain signal. Stimulation parameters are generated based on the noise reduced frequency domain signal and are transmitted to the stimulation sub-system 12.

Stimulation sub-system 12 serves to generate and apply electrical stimulation (also referred to herein as "stimulation current" and/or "stimulation pulses") to stimulation sites at the auditory nerve within the cochlea of a patient 17 in accordance with the stimulation parameters received from the sound processing sub-system 11. Electrical stimulation is provided to the patient 17 via a CI stimulation assembly 18 comprising a plurality of stimulation channels, wherein various known stimulation strategies, such as current steering stimulation or N-of-M stimulation, may be utilized.

As used herein, a "current steering stimulation strategy" is one in which weighted stimulation current is applied concurrently to two or more electrodes by an implantable cochlear stimulator in order to stimulate a stimulation site located in between areas associated with the two or more electrodes and thereby create a perception of a frequency in between the frequencies associated with the two or more electrodes, compensate for one or more disabled electrodes, and/or generate a target pitch that is outside a range of pitches associated with an array of electrodes.

As used herein, an "N-of-M stimulation strategy" is one in which stimulation current is only applied to N of M total stimulation channels during a particular stimulation frame, where N is less than M. An N-of-M stimulation strategy may be used to prevent irrelevant information contained within an audio signal from being presented to a CI user, achieve higher stimulation rates, minimize electrode interaction, and/or for any other reason as may serve a particular application.

The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp-on time, and ramp-off time of the stimulation current that is applied to the stimulation site.

Figure 3:
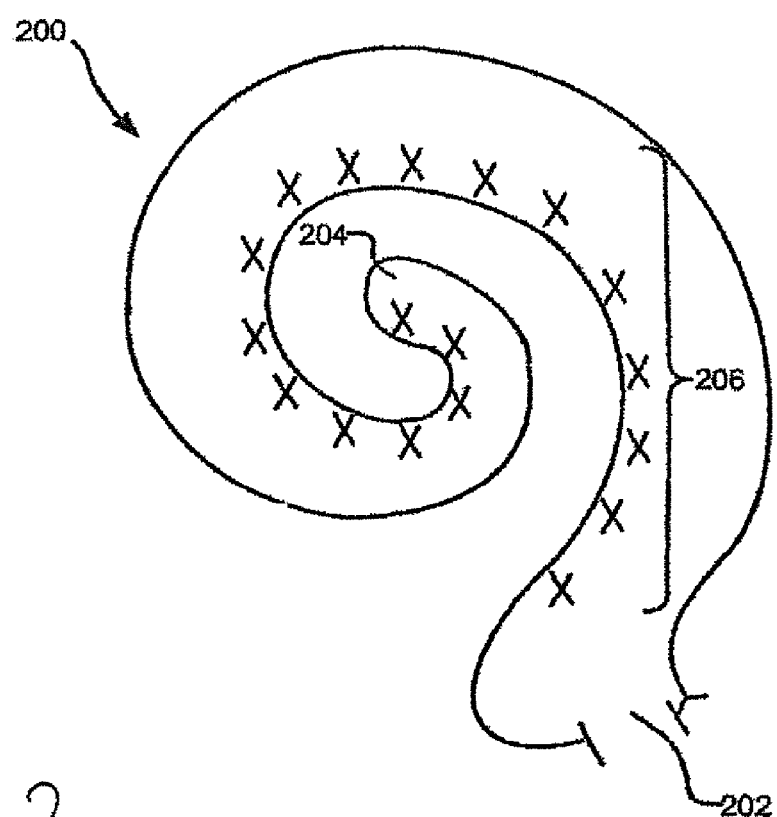
FIG. 3 is a schematic cross-sectional view of a human cochlea with marked stimulation sites.

FIG. 3 illustrates a schematic structure of the human cochlea 200. As shown in FIG. 3, the cochlea 200 is in the shape of a spiral beginning at a base 202 and ending at an apex 204. Within the cochlea 200 resides auditory nerve tissue 206 which is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 12 is configured to apply stimulation to different locations within the cochlea 200 (e.g., different locations along the auditory nerve tissue 206) to provide a sensation of hearing.

Returning to FIG. 2, sound processing subsystem 11 and stimulation subsystem 12 is configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application. In particular, the control parameters may include a frequency allocation table (FAT) which determines the respective frequency range allocated to a certain electrode.

In the example shown in FIG. 2, the stimulation sub-system 12 comprises an implantable cochlear stimulator (ICS) 14, a lead 16 and the stimulation assembly 18 disposed on the lead 16. The stimulation assembly 18 comprises a plurality of "stimulation contacts" 19 for electrical stimulation of the auditory nerve. The lead 16 may be inserted within a duct of the cochlea in such a manner that the stimulation contacts 19 are in communication with one or more stimulation sites within the cochlea, i.e. the stimulation contacts 19 are adjacent to, in the general vicinity of, in close proximity to, directly next to, or directly on the respective stimulation site.

In the example shown in FIG. 2, the sound processing sub-system 11 is designed as being located external to the patient 17; however, in alternative examples, at least one of the components of the sub-system 11 may be implantable.

In the example shown in FIG. 2, the sound processing sub-system 11 comprises a microphone 20 which captures audio signals from ambient sound, a microphone link 22, a sound processor 24 which receives audio signals from the microphone 20 via the link 22, and a headpiece 26 having a coil 28 disposed therein. The sound processor 24 is configured to process the captured audio signals in accordance with a selected sound processing strategy to generate appropriate stimulation parameters for controlling the ICS 14 and may include, or be implemented within, a behind-the-ear (BTE) unit or a portable speech processor (PSP). In the example of FIG. 2 the sound processor 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30. The link 30 may include a bidirectional communication link and/or one or more dedicated unidirectional communication links. According to an alternative embodiment, the sound processor 24 and the ICS 14 may be directly connected by wires.

Figure 4:
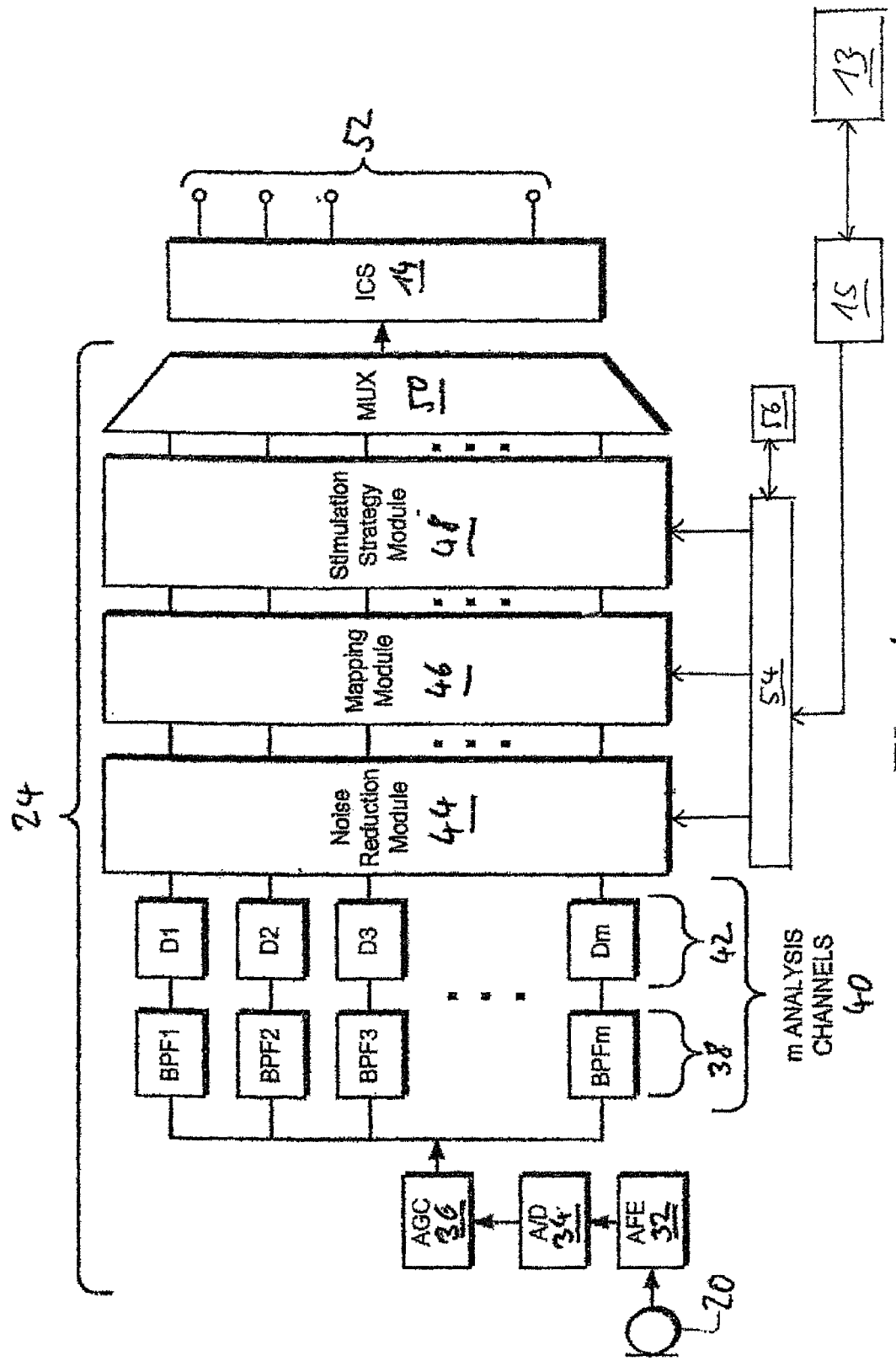
FIG. 4 is a block diagram of an example of the signal processing structure of a CI device to be used with the invention.

In FIG. 4 a schematic example of a sound processor 24 is shown. The audio signals captured by the microphone 20 are amplified in an audio front end circuitry 32, with the amplified audio signal being converted to a digital signal by an analog-to-digital converter 34. The resulting digital signal is then subjected to automatic gain control using a suitable automatic gain control (AGC) unit 36.

After appropriate automatic gain control, the digital signal is subjected to a filterbank 38 comprising a plurality of filters F1 . . . Fm (for example, band-pass filters) which are configured to divide the digital signal into m analysis channels 40, each containing a signal representative of a distinct frequency portion of the audio signal sensed by the microphone 20. For example, such frequency filtering may be implemented by applying a Discrete Fourier Transform to the audio signal and then distribute the resulting frequency bins across the analysis channels 40.

The signals within each analysis channel 40 are input into an envelope detector 42 in order to determine the amount of energy contained within each of the signals within the analysis channels 40 and to estimate the noise within each channel. After envelope detection the signals within the analysis channels 40 may be input into a noise reduction module 44, wherein the signals are treated in a manner so as to reduce noise in the signal in order to enhance, for example, the intelligibility of speech by the patient. Examples of the noise reduction module 44 are described in WO 2011/032021 A1.

The optionally noise reduced signals are supplied to a mapping module 46 which serves to map the signals in the analysis channels 40 to the stimulation channels S1 . . . Sn. For example, signal levels of the noise reduced signals may be mapped to amplitude values used to define the electrical stimulation pulses that are applied to the patient 17 by the ICS 14 via M stimulation channels 52. For example, each of the m stimulation channels 52 may be associated to one of the stimulation contacts 19 or to a group of the stimulation contacts 19.

The sound processor 24 further comprises a stimulation strategy module 48 which serves to generate one or more stimulation parameters based on the noise reduced signals and in accordance with a certain stimulation strategy (which may be selected from a plurality of stimulation strategies). For example, stimulation strategy module 48 may generate stimulation parameters which direct the ICS 14 to generate and concurrently apply weighted stimulation current via a plurality 52 of the stimulation channels S1 . . . Sn in order to effectuate a current steering stimulation strategy. Additionally or alternatively the stimulation strategy module 48 may be configured to generate stimulation parameters which direct the ICS 14 to apply electrical stimulation via only a subset N of the stimulation channels 52 in order to effectuate an N-of-M stimulation strategy.

The sound processor 24 also comprises a multiplexer 50 which serves to serialize the stimulation parameters generated by the stimulation strategy module 48 so that they can be transmitted to the ICS 14 via the communication link 30, i.e. via the coil 28.

The sound processor 24 may operate in accordance with at least one control parameter which is set by a control unit 54. Such control parameters, which may be stored in a memory 56, may be the most comfortable listening current levels (MCL), also referred to as "M levels", threshold current levels (also referred to as "T levels"), dynamic range parameters, channel acoustic gain parameters, front and back end dynamic range parameters, current steering parameters, amplitude values, pulse rate values, pulse width values, polarity values, the respective frequency range assigned to each electrode and/or filter characteristics. Examples of such auditory prosthesis devices, as described so far, can be found, for example, in WO 2011/032021 A1.

The programming unit 13 acts on the control unit 54 via the interface 15 for causing the ICS 14 and the electrode array 19 to apply a certain probe stimulus to the cochlea 200 as will be discussed in detail below.

The hearing aid 21 comprises a microphone arrangement 29 for capturing audio signals from ambient sound, an audio signal processing unit 27 for processing the captured audio signals and the loudspeaker 23 to which the processed audio signals are supplied. The programming unit 13 acts, via the interface 15, on the audio signal processing unit 27 in order to cause the loudspeaker 23 to emit probe acoustic stimulation signals supplied to the contralateral ear in a synchronized manner with regard to the probe neural stimulus applied by the CI device 10.

Hereinafter, an example of the fitting procedure will be described by reference to FIGS. 5 to 7.

In general, normal hearing persons with intact peripheral and sensual (binaural) auditory processing are able to fuse/merge dichotic presentations of vowels (for example, presentation of the first formant F1 on the left ear and presentation of the second formant F2 on the right ear), CVCs and formant transitions (for example da-ga-ba).

Figure 7:
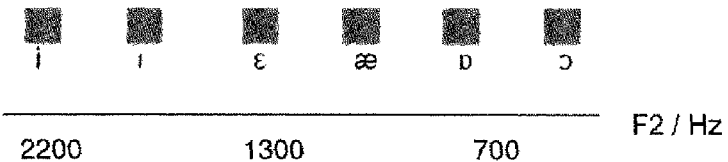
FIG. 7 is a schematic illustration of how the perceived vowel in a CVC (consonant-vowel-consonant) depends on the frequency of the second formant.

In FIG. 7 an example is schematically shown, wherein for the CVC h-vowel-d the frequency of the second formant is changed while the formant frequencies F0 and F1 are kept constant, with the formant frequency F2 is presented ipsilaterally and F0 and F1 being presented contralaterally; FIG. 7 shows how the perceived vowel of the CVC changes as a function of the second formant frequency F2.

However, CI patients using a bimodal fitting (electric and acoustic stimulation at the same ear) or a bilateral fitting (electrical stimulation at both ears) often are not able to fuse/merge dichotic presentations, or they hear a "wrong" fused percept (dichotic presentation in the bimodal case, for example, may be acoustic presentation of F0 and F1 and electric presentation of F2; dichotic presentation in the case of bilateral stimulation, for example, may be presentation of F0 and F1 at one ear and presentation of F2 at the other ear). This may happen, for instance, if the electrode array is not inserted deep enough into the cochlea and the acoustically presented frequencies (e.g. the second formant) are mapped to a different place pitch. In other words, the patient may be unable to fuse bimodal dichotic presentations in case that the pitch matching of the electrical stimulation and the acoustic stimulation is not sufficient; this applies in an analogous manner to bilateral dichotic presentations.

Typically, in case of bimodal stimulation higher frequencies can be stimulated in a more efficient manner via electrical stimulation, while lower frequencies may be stimulated in a more efficient manner via acoustic stimulation; further, the hearing loss of a patient may be different for the two ears with regard to frequency response. Thus, in order to achieve maximum benefit of bimodal and/or bilateral stimulation, the fitting parameters of the two stimulation devices should be optimized in order to optimize bimodal and/or binaural fusion capability of the patient; such fitting parameters may include frequency compression of the acoustic stimulation and the frequency allocation table (FAT) of the electrical stimulation.

Figure 5:
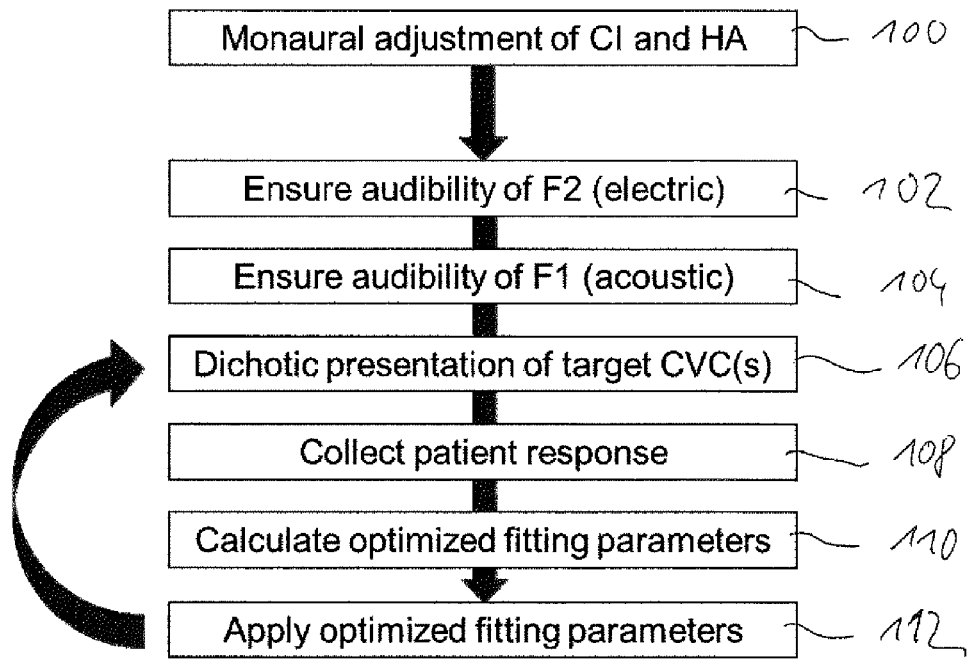
FIG. 5 is a flowchart of an example of a fitting process according to the invention.

FIG. 5 shows an example of a flow diagram of a method for optimizing bimodal fitting. In a first step 100 of a fitting procedure for a bimodal system, such as the system of FIG. 1, the CI device 10 and the hearing aid 21 undergo separate adjustment in the sense that during fitting of one of the devices the other device is not active; for a bilateral system, such as the bimodal bilateral system of FIG. 1, such separate adjustment is a monaural adjustment.

Figure 6:
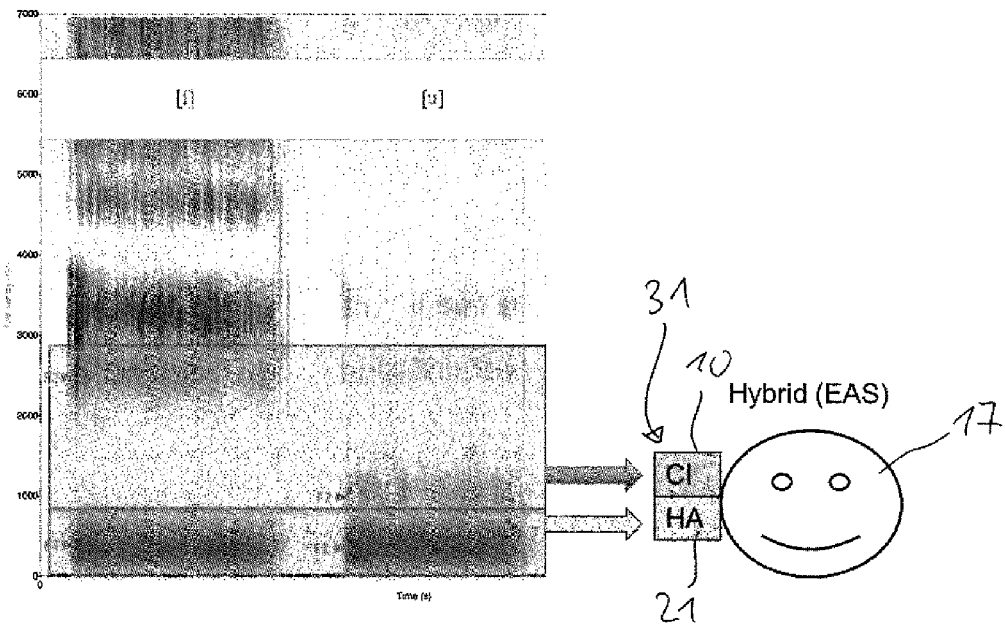
FIG. 6 is a schematic illustration of an example of how a probe neural stimulation signal and a probe second stimulation signal may be divided onto the CI device and a hearing aid.

Examples of test audio signals which may be used for dichotic fitting are shown in FIG. 6, corresponding to the vowels [i] and [u]. According to FIG. 6, the respective audio signal is divided frequency-wise into a probe neural stimulation signal comprising a second frequency range including the second formant frequencies F2 to be supplied via the CI device 10 and a first frequency range including the first formant frequencies F1 to be supplied via the hearing aid 21. In the example of FIG. 6 the first frequency region is at lower frequencies than the second frequency region. Thereby, a target speech information, which is represented in the example of FIG. 6 by the vowels [i] and [u], respectively, is divided into a probe neural stimulation signal to be applied by the CI device 10 and a second probe stimulation signal, i.e. a probe acoustic stimulation signal, to be supplied via the hearing aid 21.

This target speech information can be recognized by the patient only in case that the patient is able to merge the acoustic stimulation (in the lower frequency range) and the electrical stimulation (in the higher frequency range) into a single percept, since for correctly recognizing the vowel both the first and second formant are necessary.

For preparing such dichotic presentation of both stimuli, it is first necessary to ensure in steps 102 and 104 the audibility of the electric stimulation part of the test audio signal (namely the F2 formant) and the audibility of the acoustic stimulation part (the F1 formant) of the test audio signal, respectively. In steps 102 and 104, the electric stimulation part and the acoustic stimulation part are applied separately to the patient via the CI device 10 and the hearing aid 21, respectively.

In step 106 the test audio signal is presented in a dichotic manner by applying the neural (i.e. electric) stimulation signal via the CI device 10 and the probe acoustic stimulation signal via the hearing aid 21 in a synchronized manner to the patient.

In step 108 the response of the patient to the test audio signal is recorded or collected. To this d, the fitting device 13 may comprise a display for displaying speech information like CVCs, phonemes or words to the patient and means for allowing the user to select the respective CVC, phoneme or word matching best with the CVC, phoneme or word perceived by the patient upon the dichotic presentation of the test audio signal. For example, if the target speech information is the word or CVC "had", the fitting device 13 may display the words shown in FIG. 7 for selection by the patient ("heed", "hid", "head", "had", "hod", and "hawed").

In case that the speech information selected by the patient does not equal the target speech information (for example, the patient selects "head" instead "had"), the fitting device 13 may calculate optimized fitting parameters for at least one of the CI device 10 and the hearing aid 21 in order to compensate for the "wrong" perception. For example, in case that the frequency of the second formant F2 of the vowel as perceived by the patient is higher than the second formant frequency F2 of the vowel of the target speech information, a new FAT may be calculated for the CI device assigning higher center frequencies to the most apical electrodes.

In step 112 such optimized fitting parameters are applied to the respective devices 10, 21, and then the same test audio signal may be presented in the same dichotic manner to the patient, i.e. step 106 may be repeated with the optimized fitting parameters, followed by a repetition of the response collection step 108. In case that also with the new fitting parameters there is still a deviation of the patient's perception from the target speech information, also steps 110 and 112 may be repeated in order to start a new optimization loop, etc. Such optimization loops may be repeated until the patient's perception equals the target speech information (or until another termination criterion, such as a certain time limit) is achieved.

Alternatively, instead of such a deterministic, rule-based approach, generic optimization procedures could be used.

Preferably, the test audio signal uses synthesized phonemes in or to avoid differences in duration and pronunciation. However, also modified versions (such as by filtering, time compression and/or pitch shifting) of real speech recordings might be used.

In case that the patient has a dominant ear or that the performance of an acoustic stimulus is much better than the performance of an electric stimulus or vice versa, a masking noise may be added to the better performing stimulus (i.e. to the electric stimulus or to the acoustic stimulus), or the presentation level of the "better" stimulus may be reduced accordingly.

According to another option, the spectral resolution of the electric stimulation may be increased for the fitting procedure by activating multipolar stimulation of the CI device 10.

In order to optimize dynamic fitting parameters, such as AGC (automatic gain control) time constants, dynamic dichotic stimuli may be used, for example formant transitions (such as "ba-da-ga").

Examples of the fitting parameters which may be optimized by the present invention include, for electrical stimulation, FAT, delay, AGC (compression ratio, time constant, compression kneepoint) and the type of multipolar stimulation, and, for acoustic stimulation, the setting of the frequency compression, delay, and AGC (compression ratio, time constant, compression kneepoint).

For patients with access to a large frequency range in both ears, there would also be the option to present complete stimuli (including both F1 and F2 formants) to both ears, including "conflicting pairs", where different vowels are presented to each ear.

The dichotic fitting approach described above could be embedded into a full or partial self-fitting approach, wherein in the first step audibility of soft level sounds may be optimized by presenting soft sounds to the patient, including automatic modification of the respective fitting parameters (such as gain and CK for acoustic stimulation and T-levels and input dynamic range for electric stimulation) based on the patient's response. In a second step, comfort settings for loud sounds may be achieved in a similar manner. In a third step, loudness may be balanced across frequencies and ears. Finally, the dichotic fitting procedure may be applied to optimize cross-modal listening at intermediate sound levels.

Figure 8:
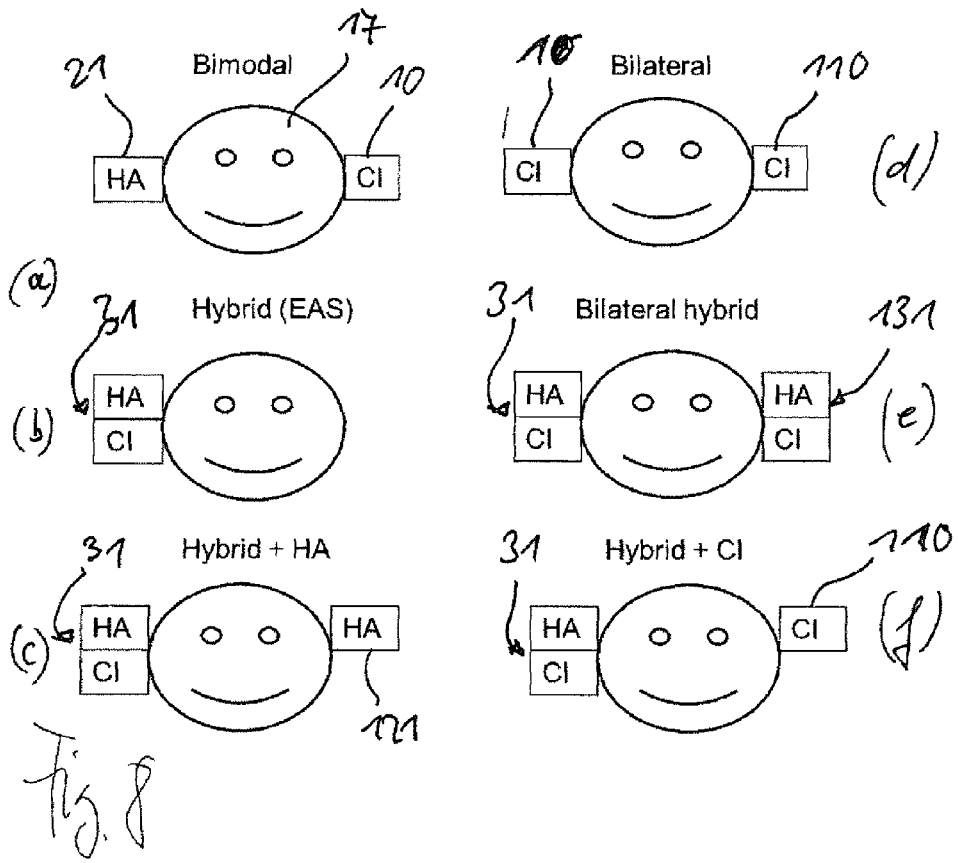
FIG. 8 is a schematic illustration of examples of system configurations according to the invention.

In FIG. 8 examples of possible stimulation configurations are shown. FIG. 8(a) corresponds to the bimodal configuration of FIG. 1 with a hearing aid 21 at one ear and a CI device 10 at the other ear. FIG. 8(b) corresponds to the hybrid configuration indicated in dashed lines in FIG. 1, comprising a hybrid device 31 including both electric and acoustic stimulation, i.e. the functionalities of the hearing aid 21 and of the CI device 10 is integrated within the hybrid device 31, with the hearing aid 21 being removed from the contralateral ear.

FIG. 8(c) shows a variant of the hybrid configuration of FIG. 8(b), wherein a hearing aid 121 is provided at the contralateral ear, in addition to the hybrid device 31 provided at the ipsilateral ear.

FIG. 8(d) shows a bilateral configuration, with a first CI device 10 being provided at the ipsilateral ear and a second CI device 110 being provided at the contralateral ear. The present invention may be applied to such bilateral systems, since, for example, the pitch of the right ear CI device and the left ear CI device may differ due to, for example, different insertion depths of the electrodes, so that the approach of the present invention may be used to improve pitch matching of the two CI devices 10, 110.

FIG. 8(e) shows a bilateral variant of the approach using the hybrid device 31 of FIG. 8(b), wherein a second hybrid device 131 is provided at the contralateral ear, in addition to the hybrid device 31 provided at the ipsilateral ear.

FIG. 8(f) shows a variant of the configuration of FIG. 8(c), wherein the hearing aid 121 provided at the contralateral ear is replaced by a second CI device 110.

Thus, in the system configurations of FIGS. 8(c), (e) and (f) there is both bimodal and bilateral stimulation. According to one example, in these cases the "single mode device" (e.g. the hearing aid 121 in FIG. 8(c)) may be provided with the same or similar stimulation signal as is supplied to the device using the same stimulation mode at the other ear (i.e. in the example of FIG. 8(c) the hearing aid of the hybrid device 31); in particular, usually the first formant will be supplied to all acoustic stimulation devices of the system and the second formant will be supplied to a electric stimulation devices of the system.

The invention claimed is:

1. A system comprising:
a first stimulation device configured to provide neural stimulation of a cochlea of a patient's ipsilateral ear;
a second stimulation device selected from the group consisting of a device configured to provide neural stimulation of the cochlea of the patient's contralateral ear, a device configured to provide acoustic stimulation of the patient's ipsilateral ear, and a device configured to provide acoustic stimulation of the patient's contralateral ear; and
a fitting device configured to adjust at least one of the first stimulation device and the second stimulation device according to a response of the patient to combined stimulation by the first stimulation device and the second stimulation device;
the first stimulation device comprising
a sound processor configured to generate a neural stimulation signal from an input audio signal; and
a cochlear implant stimulation arrangement comprising a plurality of stimulation channels configured to stimulate the ipsilateral cochlea at various stimulation sites according to the neural stimulation signal, with each stimulation channel being attributed to a certain one of the stimulation sites;
the fitting device comprising
a unit configured to cooperate with the first stimulation device and with the second stimulation device in order to generate, in a synchronized manner, a probe neural stimulation signal to be supplied to the cochlear implant stimulation arrangement and a second probe stimulation signal be supplied to the second stimulation device, with the probe neural stimulation signal and the second stimulation signal being adapted to be recognized by the patient as carrying a target speech information in case that the patient is able to correctly fuse the stimuli resulting from the probe neural stimulation signal and the second stimulation signal in the auditory cortex, with the target speech information being divided onto the probe neural stimulation signal and the second stimulation signal, and with the probe neural stimulation signal and the second stimulation signal not carrying said target speech information when perceived separately by the patient,
a unit for recording a perceptual behavioral response of the patient to the synchronized neural stimulation of the user's hearing with the probe neural stimulation signal and the second stimulation signal, and
a unit for programming the first stimulation device and/or the second stimulation device according to the recorded perceptual response.

2. The system of claim 1, wherein the target speech information is a CVC (consonant-vowel-consonant).

3. The system of claim 2, wherein the target speech information is a word or a phoneme.

4. The system of claim 3, wherein the word or phoneme is synthesized.

5. The system of claim 1, wherein the target speech information is divided onto the probe neural stimulation signal and the second stimulation signal by allocation a first spectral region to the second stimulation signal only and a second spectral region to the probe neural stimulation signal only.

6. The system of claim 5, wherein the first spectral region corresponds to a first formant of a vowel and the second spectral region corresponds to a second formant of the vowel.

7. The system of claim 1, wherein a noise signal is added to one of the probe neural stimulation signal and the second stimulation signal in order to equalize perception capability of the probe neural stimulation signal and the second stimulation signal according to the individual hearing loss.

8. The system of claim 1, wherein the probe neural stimulation signal and the second stimulation signal comprise dynamic dichotic stimuli.

9. The system of claim 8, wherein the probe neural stimulation signal and the second stimulation signal comprise formant transitions.

10. The system of claim 1, wherein the fitting device is adapted to cause the cochlear implant stimulation arrangement to apply the probe neural stimulation signal via multipolar electrode coupling.

11. The system of claim 1, wherein the second stimulation device is a device configured to provide acoustic stimulation of the patient's ipsilateral ear or a device configured to provide acoustic stimulation of the patient's contralateral ear.

12. The system of claim 11, wherein the first spectral region is at lower frequencies than the second spectral region.

13. The system of claim 1, wherein the fitting device is adapted to change the frequency allocation of the stimulation channels of the first stimulation device according to the recorded perceptual response.

14. The system of claim 1, wherein the fitting device is adapted to change the type of multipolar stimulation by the first stimulation device according to the recorded perceptual response.

15. The system of claim 1, wherein the fitting device is adapted to change a stimulation delay or at least one parameter of an automatic gain control unit of the first stimulation device according to the recorded perceptual response.

16. The system of claim 11, wherein the fitting device is adapted to change a setting of a frequency compression applied by the second stimulation device according to the recorded perceptual response.

17. The system of claim 1, wherein the fitting device is adapted to change a stimulation delay or at least one parameter of an automatic gain control unit of the second stimulation device according to the recorded perceptual response.

18. The system of claim 1, wherein the response recording comprises a display for displaying words or phonemes to the patient and means for allowing the user to select a word or phoneme matching best with the word or phoneme perceived by the patient.

19. The system of claim 18, wherein the fitting device is adapted to change the signal processing setting of the first stimulation device and/or the second stimulation device according to the deviation of the word or phoneme selected by the patient from the target word or phoneme.

20. The system of claim 11, wherein the second stimulation device is a hearing aid to be worn at the contralateral side of the patient's head.

21. The system of claim 11, wherein the neural stimulation device and the second stimulation device are integrated within a hybrid device to be worn at the ispsilateral ear.

22. The system of claim 1, wherein the cochlear implant stimulation arrangement comprises a plurality of electrodes for electrical stimulation of the cochlea, with each electrode forming one of the stimulation sites.

23. The system of claim 1, wherein the fitting device is implemented by a computer device communicating with the neural stimulation device and with the acoustic stimulation device via a programming interface.

24. A method of individually adjusting a first stimulation device configured to provide neural stimulation of a patient's cochlea of the ipsilateral ear and a second stimulation device selected from the group consisting of a device configured to provide neural stimulation of the cochlea of the patient's contralateral ear, a device configured to provide acoustic stimulation of the patient's ipsilateral ear and a device configured to provide acoustic stimulation of the patient's contralateral ear, the first stimulation device comprising a sound processor configured to generate a neural stimulation signal from an input audio signal and a cochlear implant stimulation arrangement comprising a plurality of stimulation channels configured to stimulate the cochlea at various stimulation sites according to a neural stimulation signal, with each stimulation channel being attributed to a certain one of the stimulation sites, the method comprising:

(a) generating, by a fitting device cooperating with the first stimulation device and with the second stimulation device, in a synchronized manner, a probe neural stimulation signal configured to be supplied to the cochlear implant stimulation arrangement and a second probe stimulation signal configured to be supplied to the second stimulation device, with the probe neural stimulation signal and the second stimulation signal being adapted to be recognized by the patient as carrying a target speech information in case that the patient is able to correctly fuse the stimuli resulting from the probe neural stimulation signal and the second stimulation signal in the auditory cortex, with the target speech information being divided onto the probe neural stimulation signal and the second stimulation signal, and with the probe neural stimulation signal and the second stimulation signal not carrying said target speech information when perceived separately by the patient;

(b) recording a perceptual behavioral response of the patient to the synchronized neural stimulation of the user's hearing with the probe neural stimulation signal and the second stimulation signal;

(c) programming the first stimulation device and/or the second stimulation device according to the recorded perceptual response.

25. The method of claim 24, comprising, prior to step (a), monaural separate fitting of each of the first stimulation device and the second stimulation device via the fitting device in order to ensure audibility of the probe neural stimulation signal and the second stimulation signal, when applied separately.

26. The method of claim 25, wherein the monaural separate fitting of each of the first and second stimulation device is carried out at relatively soft sound levels and at relatively loud sound levels.

27. The method of claim 26, wherein the loudness is balanced across frequencies via the fitting device.

28. The method of claim 26, wherein steps (a) to (c) are carried out at intermediate sound levels between at relatively soft sound levels and the relatively loud sound levels.

\* \* \* \* \*